(12) United States Patent
Lovett

(10) Patent No.: US 6,881,419 B2
(45) Date of Patent: Apr. 19, 2005

(54) VITAMIN FORMULATION FOR ENHANCING BONE STRENGTH

(76) Inventor: William E. Lovett, 1121 Shady Rest La., Naples, FL (US) 34103

( * ) Notice: Subject to any disclaimer, the term of this patent is extended or adjusted under 35 U.S.C. 154(b) by 0 days.

(21) Appl. No.: 10/409,208

(22) Filed: Apr. 9, 2003

(65) Prior Publication Data

US 2003/0190369 A1 Oct. 9, 2003

Related U.S. Application Data

(60) Provisional application No. 60/370,733, filed on Apr. 9, 2002, now abandoned.

(51) Int. Cl.[7] .............................................. A61K 47/00
(52) U.S. Cl. ....................................................... 424/439
(58) Field of Search ......................................... 424/439

(56) References Cited

U.S. PATENT DOCUMENTS

| | | | |
|---|---|---|---|
| 4,772,467 A | 9/1988 | Pak | 424/127 |
| 5,661,123 A | 8/1997 | Stalker et al. | 514/2 |
| 5,985,339 A | 11/1999 | Kamarei | 426/72 |
| 6,461,634 B1 * | 10/2002 | Marshall | 424/439 |
| 2001/0031744 A1 | 10/2001 | Kosbab | |

* cited by examiner

*Primary Examiner*—Alton Pryor
(74) *Attorney, Agent, or Firm*—Dykema Gossett PLLC

(57) ABSTRACT

The present invention provides a method and composition for dietary vitamin supplementation utilizing a form and dosage of vitamins and minerals for enhanced calcium absorption. The method includes the steps of providing a pharmaceutically acceptable composition including calcium citrate, and supplementing the daily dietary regimen of a subject with calcium citrate within the range of approximately 100 mg calcium to approximately 2000 mg calcium, and preferably 1000 mg calcium. The chewable form of the supplement provided herein facilitates absorption of calcium in the teeth and bones of a subject, for enhanced physiological and psychological benefits. The supplement is especially beneficial for subjects experiencing osteoporosis, arthritis, demineralization of teeth and bones, bodily pain and lack of energy, as well as for the prevention of these ailments.

7 Claims, No Drawings

VITAMIN FORMULATION FOR ENHANCING BONE STRENGTH

RELATED APPLICATIONS

This application claims benefit of priority of Provisional Application Ser. No. 60/370,733 now abandoned, filed Apr. 9, 2002.

BACKGROUND OF INVENTION a. Field of Invention

The invention relates generally to dietary supplementation, and, more particularly to a novel method and composition for dietary vitamin supplementation utilizing a form and dosage of vitamins and minerals for enhanced calcium absorption.

b. Description of Related Art

Vitamins and minerals are essential to life and vital for many functions such as the breaking down of digested food and for providing energy for each cell in the body. Many vitamins cannot be stored and therefore must be replenished on a daily basis. Minerals, which are primarily stored in bone and muscle tissue, likewise must be replenished daily. Replenishing vitamins and minerals appropriately can be a complex task and research has shown that there must be a balance of vitamins and minerals taken daily for optimal absorption. One key factor in determining a vitamin composition relates to the interaction of different vitamins and minerals. For example, a large dose of one "B" vitamin may cause a deficiency in another "B" vitamin. The same is true for minerals, which must also be taken in correct amounts and combinations to produce the synergistic effect of increasing the positive effect of each one alone.

Amongst vitamins and minerals, calcium is one of the most important minerals in a balanced diet and is vital to the formation of bones and teeth. Calcium is also important for numerous other physiological functions such as, the regulation of heartbeat, transmission of nerve impulses, lowering cholesterol, prevention of cardiovascular disease, muscular growth, repair and contractions, maintenance of energy, protein structuring of RNA and DNA, proper cell permeability, the health of skin, hair, nails and gums, improvement in blood clotting, prevention of osteoporosis and cancer, neuromuscular activity, reduction of high blood pressure, breakdown of fats, revitalization of the body from the negative effects of alcohol and tobacco, and the prevention of lead absorption in bones and teeth. For psychological functions, calcium can help prevent nervousness, depression, hyperactivity and can even help induce sleep at night.

Calcium deficiency on the other hand can lead to osteoporosis, joint pain, rheumatoid arthritis, muscle cramps, heart palpitations, tooth decay, hypertension, metal dullness and mental disorders of many types. One reason for calcium deficiency is that throughout our lives, bone is constantly being broken down and repaired. Therefore, with the formation of new bone, a constant intake of calcium is vital.

In the United States and other modern countries, nearly 80–85% of all adults are believed to be deficient in calcium intake by diet. The average "American" is estimated to be at least 25% deficient in calcium. It is reported that up to 50% of women ages 45–75 have some form of osteoporosis. For children of ages 9–18 years and adults over 50, calcium is especially needed in high concentrations. Research shows that children ages 9–18 need at least 1300 mg of calcium per day, adults ages 19–50 need at least 1000 mg per day, and adults over 50 need at least 1200 mg of calcium per day.

The daily requirements for calcium are often inhibited by the intake of soft drinks, alcohol, tobacco, almost all junk foods, processed foods, overcooked foods, smoking, caffeine in foods and canned foods. Moreover, medication, chemotherapy, lack of exercise, diets that are high in fat, sugars, excess salt, white flour and certain diseases can also inhibit the absorption of calcium. If the body does not receive calcium, it simply takes the calcium needed from bones and teeth, which store nearly 99% of the calcium in our body.

It is apparent that there are many calcium supplements on the market which aim to address the above-identified benefits of calcium. Most calcium supplements, which are in pill form and use calcium carbonate, do not dissolve well in the stomach. Calcium carbonate also does not dissolve in the mouth, and therefore does not provide direct help to teeth and oral tissues, unless food is present in the stomach. Many supplements include additives, such as antacids, that actually prevent absorption. Some vitamin companies use D-calcium-phosphate, which is insoluble and interferes with the absorption of nutrients. Therefore, unless a formula has a balance of vitamins and minerals, there will be little or no absorption, which could lead to further imbalance.

In most supplement formulas, 10–40% of calcium is elemental calcium, which is the actual absorbable portion. Thus, a supplement dosage of 1000 mg may only yield a small absolute amount of absorbable calcium. If this absorbable calcium is not in the correct formula, it will not be absorbed properly, or in some cases, no absorption may result.

Other than in pill form, calcium may also be taken in liquid form. Whereas liquid calcium may be swallowed for the bones and the body, only liquid calcium that is rinsed may be used for absorption into tooth enamel. For liquid calcium, only citrate can be absorbed in the mouth.

Today's research has made significant breakthroughs in the identification of vitamins, minerals and amino acids that are necessary for the proper absorption of calcium into cells. Since bones are constantly being broken down and reformed, cell permeability, transfer, apposition or usage by bones, teeth and joints for replacement is dependent upon many elements for the enhanced absorption and utilization of calcium by the body. Research and analysis performed herein have determined that none of the multi-vitamin formulas available on the market contain all of the nutrients needed by the body, and especially nutrients in the correct combination and dosage for optimal calcium absorption. Accordingly, there remains a need for a novel dietary vitamin supplement which utilizes a form and dosage of vitamins and minerals for enhanced calcium absorption.

SUMMARY OF INVENTION

The invention aims to overcome the drawbacks of the above-identified multi-vitamin formulas available on the market by providing a novel method and composition (hereinafter designated L3-Multi-Vitamin Supplement) for dietary vitamin supplementation.

Thus, an aspect of the present invention is to provide a novel L3-Multi-Vitamin Supplement which is balanced to increase metabolism of calcium, increase absorption thereof into blood, decrease excretion of calcium, increase absorption of calcium into teeth and bones, aid in formation of connective tissue for strength and flexibility of bones, increase the proper action of normal new bone formation, and provide abundant calcium for all bodily functions.

Another aspect of the present invention is to provide a L3-Multi-Vitamin Supplement that will provide energy and healthy functions for the entire body.

Yet another aspect of the present invention is to provide a L3-Multi-Vitamin Supplement which is chewable to provide direct help to the teeth, and which is directly absorbed with or without food.

Specifically, the present invention provides a method for dietary calcium supplementation, as well as a multi-vitamin supplement for the dietary calcium supplementation. The method, which utilizes the multi-vitamin supplement, includes the step of providing a pharmaceutically acceptable composition including calcium citrate. The method further includes the step of supplementing a daily dietary regimen of a subject with calcium citrate comprising from approximately 100 mg calcium to approximately 2000 mg calcium, from approximately 50 mg magnesium to approximately 1000 mg magnesium, from approximately 50 mg to approximately 1000 mg of phosphorous, from approximately 40 IU to approximately 800 IU of Vitamin $D^3$ and from approximately 0.3 mg to approximately 6 mg of boron. The preferred dosages for the supplement may include calcium citrate including approximately 1000 mg of calcium, approximately 100 mg magnesium, approximately 500 mg of phosphorous, approximately 400 IU of Vitamin $D^3$, and approximately 3 mg of boron.

For the method and multi-vitamin supplement described above, the supplement may include the following ranges of dosages: from approximately 200 IU to approximately 4000 IU of Vitamin A; from approximately 50 mg to approximately 1000 mg of Vitamin C; from approximately 40 IU to approximately 800 IU of Vitamin E; from approximately 10 mcg to approximately 200 mcg of Vitamin K; from approximately 5 mg to approximately 100 mg of Thiamin; from approximately 1.5 mg to approximately 30 mg of Riboflavin; from approximately 5 mg to approximately 100 mg of Niacin; from approximately 5 mg to approximately 100 mg of Vitamin $B^6$; from approximately 20 mcg to approximately 400 mcg of Vitamin $B^{12}$; from approximately 5 mg to approximately 100 mg of Pantothenic Acid; from approximately 40 mcg to approximately 800 mcg of Folate; from approximately 30 mg to approximately 600 mcg of Biotin; from approximately 10 mg to approximately 200 mg of Potassium; from approximately 5 mg to approximately 100 mg of Zinc; from approximately 20 mcg to approximately 400 mcg of Selenium; from approximately 0.2 mg to approximately 4 mg of Copper; from approximately 0.3 mg to approximately 6 mg of Manganese; from approximately 1 mg to approximately 20 mg of Vanadium; from approximately 0.1 mg to approximately 2 mg of Silica; from approximately 5 mg to approximately 100 mg of L-Lysine; from approximately 50 mg to approximately 1000 mg of Bioflavanoid Complex; from approximately 20 mg to approximately 400 mg of Ipriflavone; and from approximately 9 mg to approximately 180 mg of Soy Isoflavones.

For the method and multi-vitamin supplement described above, the supplement may include the following preferable dosages: approximately 2000 IU of Vitamin A; approximately 500 mg of Vitamin C; approximately 400 IU of Vitamin E; approximately 100 mcg of Vitamin K; approximately 50 mg of Thiamin; approximately 15 mg of Riboflavin; approximately 50 mg of Niacin; approximately 50 mg of Vitamin $B^6$; approximately 200 mcg of Vitamin $B^{12}$; approximately 50 mg of Pantothenic Acid; approximately 400 mcg of Folate; approximately 300 mcg of Biotin; approximately 100 mg of Potassium; approximately 50 mg of Zinc; approximately 200 mcg of Selenium; approximately 2 mg of Copper; approximately 3 mg of Manganese; approximately 10 mg of Vanadium; approximately 1 mg of Silica; approximately 50 mg of L-Lysine; approximately 500 mg of Bioflavanoid Complex; approximately 200 mg of Ipriflavone; and approximately 90 mg of Soy Isoflavones.

The method and multi-vitamin supplement described above may be formulated for a subject having osteoporosis, arthritis, demineralization of teeth and bones, bodily pain, and lack of energy, as well as for the prevention of these ailments. The supplement may be provided in chewable form for facilitating absorption in teeth and bones of the subject.

The invention further provides a method for dietary calcium supplementation, as well as a multi-vitamin supplement for the dietary calcium supplementation. The method, which utilizes the multi-vitamin supplement includes the step of providing a pharmaceutically acceptable composition including calcium citrate. The method further includes the step of supplementing a daily dietary regimen of a subject with calcium citrate comprising from approximately 10% to approximately 200% of the daily value requirement for calcium citrate, from approximately 12% to approximately 240% of the daily value requirement for magnesium, from approximately 10% to approximately 200% of the daily value requirement for Vitamin $D^3$ and from approximately 5% to approximately 100% of the daily value requirement for Phosphorous, the daily value being based on a 2,000 calorie diet. The preferred values for the supplement may include calcium citrate including approximately 100% of the daily value requirement for calcium, approximately 120% of the daily value requirement for magnesium, approximately 100% of the daily value requirement for Vitamin $D^3$, and approximately 50% of the daily value requirement for Phosphorous.

For the method and multi-vitamin supplement described above, the supplement may include the following ranges of values: from approximately 4% to approximately 80% of the daily value requirement for Vitamin A; from approximately 83% to approximately 1660% of the daily value requirement for Vitamin C; from approximately 133% to approximately 2660% of the daily value requirement for Vitamin E; from approximately 112% to approximately 2240% of the daily value requirement for Vitamin K; from approximately 333% to approximately 6660% of the daily value requirement for Thiamin; from approximately 88% to approximately 1760% of the daily value requirement for Riboflavin; from approximately 25% to approximately 500% of the daily value requirement for Niacin; from approximately 250% to approximately 5000% of the daily value requirement for Vitamin $B^6$; from approximately 333% to approximately 6660% of the daily value requirement for Vitamin $B^{12}$; from approximately 50% to approximately 1000% of the daily value requirement for Pantothenic Acid; from approximately 10% to approximately 200% of the daily value requirement for Folate; from approximately 10% to approximately 200% of the daily value requirement for Biotin; from approximately 0.3% to approximately 6% of the daily value requirement for Potassium; from approximately 33% to approximately 660% of the daily value requirement for Zinc; from approximately 28% to approximately 560% of the daily value requirement for Selenium; from approximately 10% to approximately 200% of the daily value requirement for Copper; and from approximately 15% to approximately 300% of the daily value requirement for Manganese.

For the method and multi-vitamin supplement described above, the supplement may include the following preferable values: approximately 40% of the daily value requirement for Vitamin A; approximately 830% of the daily value requirement for Vitamin C; approximately 1330% of the daily value requirement for Vitamin E; approximately 120% of the daily value requirement for Vitamin K; approximately 3330% of the daily value requirement for Thiamin; approximately 880% of the daily value requirement for Riboflavin; approximately 250% of the daily value requirement for Niacin; approximately 2500% of the daily value requirement for Vitamin $B^6$; approximately 3330% of the daily value requirement for Vitamin $B^{12}$; approximately 500% of the daily value requirement for Pantothenic Acid; approximately 100% of the daily value requirement for Folate; approximately 100% of the daily value requirement for Biotin; approximately 3% of the daily value requirement for Potassium; approximately 330% of the daily value requirement for Zinc; approximately 280% of the daily value requirement for Selenium; approximately 100% of the daily value requirement for Copper; and approximately 150% of the daily value requirement for Manganese.

Additional features, advantages, and embodiments of the invention may be set forth or apparent from consideration of the following detailed description and claims. Moreover, it is to be understood that both the foregoing summary of the invention and the following detailed description are exemplary and intended to provide further explanation without limiting the scope of the invention as claimed.

DETAILED DESCRIPTION OF THE PREFERRED EMBODIMENT

The present invention provides a method and composition (hereinafter designated L3-Multi-Vitamin Supplement) for dietary vitamin supplementation utilizing a form and dosage of vitamins and minerals for enhanced calcium absorption.

From infancy to old age, calcium is emphasized as an important building block and is the most abundant mineral in the human body. Calcium provides strength to bones and teeth, in which nearly 99% of the body's calcium is stored. The remaining calcium, which is in the bloodstream, assists in muscle contraction, blood clotting and nerve impulse management. It also assists in the regulation of heartbeat, and assists with short-term memory. If calcium is not provided to the body by means of natural foods or supplements, the body will "steal" calcium from the bones to ensure that the required amount of calcium is present in the bloodstream. If the body is not given enough calcium from natural foods or supplements and is forced to take it from the bones and teeth, a "negative calcium balance" will result.

As discussed above, the recommended daily allowance of calcium for adults is approximately 1000 mg elemental calcium. Adult subjects however usually get only on the order of 500–600 mg of calcium per day from natural food sources, such as dairy products and the like. For an average "American" diet, it is quite difficult to get all of the daily required calcium from a diet of natural foods. Thus a calcium supplement is required to help a subject obtain the required 1000 mg or more of calcium per day. The effectiveness of a calcium supplement is however highly dependent on the dosage of vitamins and minerals, which must be determined through research and testing for providing the maximum benefit.

Sources of calcium loss in the body include urine, sweat, feces etc. When the body becomes deficient of calcium, a key result is bone mass loss. In post-menopausal women particularly, calcium absorption drops off after menopause, which results in bone mass loss. Over thirty (30) million Americans now suffer from low bone mass disease, which can lead to fractures, complications and eventual long-term hospitalization. This low bone mass is caused by a lack of calcium in the diet.

In monetary terms, calcium has immense benefits to public health in general. For example, maintaining proper calcium levels prevents tooth and bone decay, the treatment of which costs the United States over $10 billion per year in osteoporosis related research and treatment. Recent studies by a Harvard University team indicated that raising calcium levels to the recommended daily amount could also lower the risk of some types of colon cancer by 50%, thus expanding the impact of calcium to many areas of human life.

For healthy teeth, calcium and phosphorous in the saliva are a key part of the remineralization process along with fluoride. Since the mouth is normally acidic and acid breaks down teeth, use of calcium and phosphorous and other such minerals act to neutralize some of this acidity and allow topically placed (not injected) fluoride to absorb the calcium and phosphorous. However, subjects with dry mouth don't have the calcium and phosphorous needed, as well as enough saliva there to wash teeth properly. Thus, subjects with dry mouth or low calcium levels (or both) miss out on this benefit and run a higher caries risk (tooth decay) that often can rapidly transform a healthy mouth into a mouth full of decay requiring major restorative work.

As discussed above, studies show that half of the American population is estimated to consume less than 600 mg of calcium daily. Americans typically get about 75% of their dietary calcium from dairy products such as milk, yogurt, cheese, etc. However, recent research from the Physicians Health Study at Harvard University indicates that the most common dietary calcium source (dairy products) is linked to increased risk of prostate cancer.

For women, hormone replacement that once helped women absorb calcium after menopause is now being discontinued because of side effects. This further creates a new need for what research shows is a 500 mg per/day calcium gap due to the discontinuation of hormone replacement.

If calcium is taken in supplement form, as previously emphasized, the dosage must be in the right form and quantity, and must be tailored to avoid side effects. Supplemental calcium must also be in the right combination of vitamins and minerals to support absorption and use by the body. For dental benefits, the calcium should preferably be in chewable form for ensuring maximum absorption.

With regard to the form of calcium, calcium carbonate and calcium phosphate are not as attractive as calcium citrate. Calcium carbonate must be taken with food to help reduce side effects (i.e. upset stomach or gas) and encourage absorption (i.e. food causes HCL acid to be produced, which enhances absorption for calcium carbonate). Some reports have indicated the presence of lead in some calcium carbonate supplements, although the quantity is below legal thresholds. However, the use of calcium carbonate is the cheapest approach and therefore most prevalent on the market. The use of calcium carbonate in antacid products is particularly questionable, given that the carbonate form needs acid to be absorbed, but a subject ends up taking antacid at the same time.

Calcium phosphate is sometimes touted as an option "closest to the body's natural bone" because bones contain calcium and phosphorus. However, in practice, the body has a harder time breaking down calcium phosphate in a pharmaceutical form.

Because calcium carbonate and calcium phosphate have a higher percentage of elemental calcium in them than calcium citrate (40% vs. 21%), many calcium supplements are marketed by boasting "the most calcium per ill." In fact, all this claim means is that an individual has to consume more calcium citrate to get a same net 1000 mg of elemental calcium, not that the carbonate form is somehow better or stronger. Using a chewable pill makes this difference easier to address because there is less concern about swallowing more or larger pills.

Due to the above-identified drawbacks of calcium carbonate and calcium phosphate, calcium citrate is considered to be the best calcium supplement for the following reasons. Calcium citrate has the highest bioavailabiiity and does not need stomach acid to help absorption. Calcium citrate has been shown in some studies to be better absorbed than calcium carbonate and does not require food taken therewith. It also has a 27% higher absorption rate than calcium carbonate when both are taken on an empty stomach and 22% higher absorption rate versus calcium carbonate when both are taken with food. Calcium citrate is also the only form of calcium that can be absorbed without stomach acid, which means it is the only form effective for absorption in the mouth, thus providing obvious dental benefits, as discussed herein.

In addition to calcium, the human body needs the right combination and form of vitamins and minerals for optimal supplementation. For example, using a chewable form of calcium that can be taken without food allows a person to take a supplement anytime and anywhere, thus increasing the chance of consistent usage. Chewing up the supplement provides instant breakdown and aids in getting calcium into the bloodstream. Chewing a supplement in the mouth, instead of swallowing a dissolved solution, also ensures maximum benefit for dental health as well.

Based upon the above-identified factors, the description, benefits and basis for utilization of the components for the L3-Multi-Vitamin Supplement according present invention will now be discussed in detail. The components and the benefits thereof, described below, include the following vitamins and minerals: magnesium, boron, zinc, phosphorus, L-lysine, potassium, manganese, copper, Vitamin A, Vitamin C, Vitamin $D^3$, Vitamin E, Vitamin K, ipriflavone, Vitamin $B^1$, Vitamin $B^2$, Vitamin $B^3$, Vitamin $B^5$, Vitamin $B^6$, Vitamin $B^{12}$, silicon, selenium, vanadium, bioflavonoids and isoflavonoids.

Magnesium (phosphate dibasic) is necessary for calcium (citrate) and potassium uptake (dispersion and utilization) and energy production, as well as for the correct function of osteoblast (bone building cells). Studies show that 80% of Americas do not get the required daily amount of magnesium. Studies indicate a 2:1 balance of calcium to magnesium is optimal.

Potassium (phosphate dibasic) improves cell membrane transfer of nutrients.

Phosphorous is required for merging calcium into bone. Without a corresponding increase in phosphorus intake, people taking calcium supplements run the risk of a phosphorus deficiency that would reduce bone mass at the end. Some studies indicate supplements should contain a 2:1 balance of calcium to phosphorus for proper balance and benefit.

Manganese is an essential mineral for skeletal development.

Boron and L-lysine improve calcium absorption, with L-lysine further improving connective tissue strength. Boron further assists in transfer of calcium from the bloodstream to bone structure, and helps prevent loss of calcium in urine.

Zinc (citrate) is important for calcium uptake, the function of the immune system and proper bone maintenance. Studies indicate that the American diet provides under 60% of the required daily amount for this mineral.

Silica is important for calcium uptake and the synthesis of collagen (connective bone tissue).

Copper (citrate) aids in the formation of bones and skeletal mineralization.

Selenium (sodium selenate) is a vital antioxidant, which acts with Vitamin E for the production of antibodies and the maintenance of a healthy heart, liver and tissue elasticity.

Vanadium (citrate) is beneficial in the formation of bones and teeth, and for growth and reproduction.

Vitamin $D^3$ (cholecalciterol) is one of the most important factors in calcium absorption.

Vitamin K (phylloquinone) is essential for the production of bone protein. It also acts as a receptor for the formation of calcium ions and reduces urinary calcium loss.

Vitamin E (d-alpha tocopheryl acetate) aids in the use of Vitamin A and vital antioxidants necessary for tissue repair.

Vitamin C (ascorbic acid) is important for collagen and connective tissue formation, as well as for the maintenance of healthy gums.

Bioflavonoids are essential for the absorption of Vitamin C.

Soy isoflavonoids promote bone mass and protect antioxidant vitamins from oxidate damage.

Vitamin A (retinol palmitate) retards the aging process, and is essential for the maintenance and repair of epithelial tissue and bone formation.

Vitamin $B^1$ enhances circulation and is important for digestion.

Vitamin $B^2$ is necessary for red blood cell formation, antibody production and cell respiration and growth.

Vitamin $B^3$ is necessary for proper circulation, the functioning of the nervous system, metabolism and for proper digestion.

Vitamin $B^5$ is an anti-stress vitamin which aids in vitamin utilization, energy production and the production of neurotransmitters.

Vitamin $B^6$ (pyridoxine hydrochloride) is important for most of the bodily functions, and especially for mental and physical health.

Vitamin $B^{12}$ (cyanocobalamine) is needed to prevent anemia, and for proper digestion, absorption of foods, synthesis of protein and metabolism. Vitamin $B^{12}$ also provides strength to protein in bone tissue.

The above-identified minerals and vitamins, which are useful for the L3-Multi-Vitamin Supplement according present invention, are essential to human life and good health. Of the above-identified vitamins and minerals, the usage of calcium (citrate), magnesium, phosphorous, boron and Vitamin $D^3$, are essential to the benefits of the L3-Multi-Vitamin Supplement discussed herein. The remaining vitamins and minerals enhance the effect of the essential elements to further provide benefits to the entire human body.

With regard to the human body, since many of these minerals and vitamins can only be used when available, they must be constantly replenished. As discussed above, during periods of absence or shortage, those vitamins and minerals stored in the bones, teeth and muscle tissue are slowly depleted. Thus, by means of a process known as "roofing," lack of essential vitamins and minerals can greatly hasten the aging process and produce poor health, lack of vitality and cause lack of energy for everyday life.

In addition to the benefits discussed above, the above-identified vitamins and minerals (also referred to as nutrients hereinafter) provide energy, which helps prevent fatigue and also protects the immune system against colds and flu. Nutrients also help prevent cancer, maintain good mental health, facilitate dealing with stress, and help prevent memory loss, Alzheimer's disease and insomnia. They guard against infection in organs such as the heart by helping to prevent heart disease and the build-up of bad cholesterol. Vitamins and minerals further protect the human body against the toxin "homocystine," a chemical which attacks the heart and allows deposits of cholesterol around the heart. Nutrients also aid in the lubrication of joints, prevent glucose intolerance and abscesses. They aid the skin by reducing wrinkles, skin disorders, slowing the aging process, age spots, acne, and aid in the formation of skin proteins.

For the vision, nutrients help prevent night blindness, cataracts and aid in the overall health of the eyes.

For digestion, vitamins and minerals aid in the normal digestion of foods, help heal ulcers and prevent diarrhea. They also aid in the tasting of foods and the prevention of a sore tongue.

The above-identified nutrients also facilitate blood clotting, prevent salt retention, edema, headaches and strokes. They also aid in the synthesis of sex hormones and reproduction, regulation of muscle tone and composition of body fluids, unwanted weight loss and unhealthy weight gain. They are essential in the utilization of many other vitamins and minerals, the synergistic activity of all nutrients, and the absorption and prevention of cell damage and cell permeability. They are also a vital catalyst for enzyme activity, oxidation and metabolism.

Based upon the above-identified description of the components for the L3-Multi-Vitamin Supplement according present invention, the preferred dosage for the L3-Multi-Vitamin Supplement are listed in Table 1, which specifically lists the average adult daily dose per tablet of the L3-Multi-Vitamin Supplement. Those skilled in the art will appreciate in view of this disclosure that the L3-Multi-Vitamin Supplement of the present invention may be provided in many forms, including pill, capsule, gel etc., without departing from the scope of this disclosure.

TABLE 1

Preferred Dosage for Exemplary
L3-Multi-Vitamin Supplement

| Formula Components | Average Adult Daily Dose (dose/day) |
|---|---|
| Vitamin A (Retinol Palmitate) | 2000 IU |
| Vitamin C (Ascorbic Acid) | 500 mg |
| Vitamin E (D-alpha Tocopheryl Acetate) | 400 IU |
| Vitamin $D^3$ (Cholecalciterol) | 400 IU |
| Vitamin K (Phylloquinone) | 100 mcg |
| Thiamin (Hydrochloride) | 50 mg |
| Riboflavin | 15 mg |
| Niacin (Niacinamide) | 50 mg |
| Vitamin $B^6$ (Pyridoxine Hydrochloride) | 50 mg |
| Vitamin $B^{12}$ (Cyanocobalamine) | 200 mcg |
| Pantothenio Acid (Calcium Pantothenate) | 50 mg |
| Folate | 400 mcg |
| Biotin | 300 mcg |
| Calcium (Citrate) | 1000 mg |

TABLE 1-continued

Preferred Dosage for Exemplary
L3-Multi-Vitamin Supplement

| Formula Components | Average Adult Daily Dose (dose/day) |
|---|---|
| Potassium (Phosphate Dibasic) | 100 mg |
| Phosphorous (Dipotassium Phosphate and Magnesium Phosphate Dibasic) | 500 mg |
| | 15 mg |
| Magnesium (Phosphate Dibasic) | 500 mg |
| Zinc (Citrate) | 50 mg |
| Selenium (Sodium Selenate) | 200 mcg |
| Copper (Citrate) | 2 mg |
| Manganese (Citrate) | 3 mg |
| Boron (Citrate) | 3 mg |
| Vanadium (Citrate) | 10 mg |
| Silica | 1 mg |
| L-Lysine | 50 mg |
| Bioflavanoid Complex | 500 mg |
| Ipriflavone | 200 mg |
| Soy Isoflavones | 90 mg |
| Sucrose | * |
| Xylitol | * |
| Fructose | * |
| Natural Flavor | * |
| Magnesium Stearate | * |
| Citric Acid | * |
| Acesulfame Potassium | * |
| Suoralose | * |
| Ethyl Maltol | * |

*Daily Dose not established

The allowable dosage ranges for the L3-Multi-Vitamin Supplement, which provide enhanced calcium absorption, are listed in Table 2, which specifically lists the average adult daily dose per tablet of the L3-Multi-Vitamin Supplement. It should be noted that the dosage ranges provide a range of a vitamin or mineral which may be used in a L3-Multi-Vitamin Supplement, without diminishing the calcium absorption capabilities.

TABLE 2

Allowable Dosage Ranges for
Exemplary L3-Multi-Vitamin Supplement

| Formula Components | Average Adult Daily Dose (dose/day) |
|---|---|
| Vitamin A (Retinol Palmitate) | 200–4000 IU |
| Vitamin C (Ascorbic Acid) | 50–1000 mg |
| Vitamin E (D-alpha Tocopheryl Acetate) | 40–800 IU |
| Vitamin $D^3$ (Cholecalciterol) | 40–800 IU |
| Vitamin K (Phylloquinone) | 10–200 mcg |
| Thiamin (Hydrochloride) | 5–100 mg |
| Riboflavin | 1.5–30 mg |
| Niacin (Niacinamide) | 5–100 mg |
| Vitamin $B^6$ (Pyridoxine Hydrochloride) | 5–100 mg |
| Vitamin $B^{12}$ (Cyanocobalamine) | 20–400 mcg |
| Pantothenio Acid (Calcium Pantothenate) | 5–100 mg |
| Folate | 40–800 mcg |
| Biotin | 30–600 mcg |
| Calcium (Citrate) | 100–2000 mg |
| Potassium (Phosphate Dibasic) | 10–200 mg |
| Phosphorous (Dipotassium Phosphate and Magnesium Phosphate Dibasic) | 50–1000 mg |
| | 1.5–30 mg |
| Magnesium (Phosphate Dibasic) | 50–1000 mg |
| Zinc (Citrate) | 5–100 mg |
| Selenium (Sodium Selenate) | 20–400 mcg |
| Copper (Citrate) | 0.2–4 mg |
| Manganese (Citrate) | 0.3–6 mg |
| Boron (Citrate) | 0.3–6 mg |
| Vanadium (Citrate) | 1–20 mg |
| Silica | 0.2–2 mg |
| L-Lysine | 5–100 mg |

TABLE 2-continued

Allowable Dosage Ranges for
Exemplary L3-Multi-Vitamin Supplement

| Formula Components | Average Adult Daily Dose (dose/day) |
|---|---|
| Bioflavanoid Complex | 50–1000 mg |
| Ipriflavone | 20–400 mg |
| Soy Isoflavones | 9–180 mg |
| Sucrose | * |
| Xylitol | * |
| Fructose | * |
| Natural Flavor | * |
| Magnesium Stearate | * |
| Citric Acid | * |
| Acesulfame Potassium | * |
| Suoralose | * |
| Ethyl Maltol | * |

*Daily Dose not established

The preferred dosage values for the L3-Multi-Vitamin Supplement are listed in Table 3, which specifically lists the average adult daily value per tablet of the L3-Multi-Vitamin Supplement, based upon a 2000 calorie diet.

TABLE 3

Preferred Dosage Values for
Exemplary L3-Multi-Vitamin Supplement

| Formula Components | Average Adult Daily Value (%) |
|---|---|
| Vitamin A (Retinol Palmitate) | 40% |
| Vitamin C (Ascorbic Acid) | 830% |
| Vitamin E (D-alpha Tocopheryl Acetate) | 1330% |
| Vitamin $D^3$ (Cholecalciterol) | 100% |
| Vitamin K (Phylloquinone) | 120% |
| Thiamin (Hydrochloride) | 3330% |
| Riboflavin | 880% |
| Niacin (Niacinamide) | 250% |
| Vitamin $B^6$ (Pyridoxine Hydrochloride) | 2500% |
| Vitamin $B^{12}$ (Cyanocobalamine) | 3330% |
| Pantothenic Acid (Calcium Pantothenate) | 500% |
| Folate | 100% |
| Biotin | 100% |
| Calcium (Citrate) | 100% |
| Potassium (Phosphate Dibasic) | 3% |
| Phosphorous (Dipotassium Phosphate and Magnesium Phosphate Dibasic) | 50% |
| Magnesium (Phosphate Dibasic) | 120% |
| Zinc (Citrate) | 330% |
| Selenium (Sodium Selenate) | 280% |
| Copper (Citrate) | 100% |
| Manganese (Citrate) | 150% |
| Boron (Citrate) | * |
| Vanadium (Citrate) | * |
| Silica | * |
| L-Lysine | * |
| Bioflavanoid Complex | * |
| Ipriflavone | * |
| Soy Isoflavones | * |
| Sucrose | * |
| Xylitol | * |
| Fructose | * |
| Natural Flavor | * |
| Magnesium Stearate | * |
| Citric Acid | * |
| Acesulfame Potassium | * |
| Suoralose | * |
| Ethyl Maltol | * |

*Daily Value not established

The allowable dosage value range for the L3-Multi-Vitamin Supplement, which provide enhanced calcium absorption, are listed in Table 4, which specifically lists the average adult daily value per tablet of the L3-Multi-Vitamin Supplement. As discussed above for Table 2, it should be noted that the dosage values provide a values of a vitamin or mineral which may be used in a L3-Multi-Vitamin Supplement, without diminishing the calcium absorption capabilities.

TABLE 4

Allowable Dosage Values for
Exemplary L3-Multi-Vitamin Supplement

| Formula Components | Average Adult Daily Value (%) |
|---|---|
| Vitamin A (Retinol Palmitate) | 4–80% |
| Vitamin C (Ascorbic Acid) | 83–1660% |
| Vitamin E (D-alpha Tocopheryl Acetate) | 133–2660% |
| Vitamin $D^3$ (Cholecalciterol) | 10–200% |
| Vitamin K (Phylloquinone) | 112–2240% |
| Thiamin (Hydrochloride) | 333–6660% |
| Riboflavin | 88–1760% |
| Niacin (Niacinamide) | 25–500% |
| Vitamin $B^6$ (Pyridoxine Hydrochloride) | 250–5000% |
| Vitamin $B^{12}$ (Cyanocobalamine) | 333–6660% |
| Pantothenic Acid (Calcium Pantothenate) | 50–1000% |
| Folate | 10–200% |
| Biotin | 10–200% |
| Calcium (Citrate) | 10–200% |
| Potassium (Phosphate Dibasic) | 0.3–6% |
| Phosphorous (Dipotassium Phosphate and Magnesium Phosphate Dibasic) | 5–100% |
| Magnesium (Phosphate Dibasic) | 12–240% |
| Zinc (Citrate) | 33–660% |
| Selenium (Sodium Selenate) | 28–560% |
| Copper (Citrate) | 10–200% |
| Manganese (Citrate) | 15–300% |
| Boron (Citrate) | * |
| Vanadium (Citrate) | * |
| Silica | * |
| L-Lysine | * |
| Bioflavanoid Complex | * |
| Ipriflavone | * |
| Soy Isoflavones | * |
| Sucrose | * |
| Xylitol | * |
| Fructose | * |
| Natural Flavor | * |
| Magnesium Stearate | * |
| Citric Acid | * |
| Acesulfame Potassium | * |
| Suoralose | * |
| Ethyl Maltol | * |

*Daily Value not established

Based upon the above-identified composition and dosage of vitamins and minerals, the L3-Multi-Vitamin Supplement of the present invention provides the optimal calcium solution for teeth, bones gums and total body heath. The L3-Multi-Vitamin Supplement specifically uses calcium citrate to achieve maximum absorption and bioavailability, to avoid stomach upset and to avoid the need for the Supplement to be taken with food. The L3-Multi-Vitamin Supplement uses the purest ingredients of highest quality, and delivers the daily requirement of 1000 mg of elemental calcium. It also provides the optimal blend of other vitamins and minerals to ensure maximum calcium absorption and use, as well as healthy gums and total body health. The chewable form provides maximum absorption, easy usage, and dental health benefits.

With specific regard to dental health benefits, when used with a fluoride rinse, the L3-Multi-Vitamin Supplement provides a highly effective combination to ensure maximum remineralization. For subjects with dry mouth (xerostomia) symptoms, the L3-Multi-Vitamin Supplement will provide a source of remineralization, not present naturally from saliva for certain subjects. It should be noted that such dry mouth is not uncommon in many subjects, based upon a recent Tufts University research which highlighted that over 500 drugs can cause dry mouth leading to a ten-fold increase in harmful mouth bacteria. For older subjects who in general need more daily calcium to ensure the body does not steal it from bones and teeth, the L3-Multi-Vitamin Supplement will provide an optimal source of such additional calcium. Remineralization using fluoride combined with the calcium in saliva can help prevent and even reverse decay in teeth that has not progressed too far.

The following six exemplary case studies are included to further describe preferred embodiments of the present invention and are not intended to limit the invention unless specifically indicated herein. The exemplary case studies utilize subjects ranging from fifty-one (51) to eighty-three (83) years of age. In each of the exemplary case studies, the subjects were prescribed the specified dosage of the L3-Multi-Vitamin Supplement described below, and including the compositions of vitamins and minerals listed in Table 1.

Case Study-1

Remineralization and Bone Enhancement

A fifty-five (55) year old white female subject, diagnosed with osteoporosis and rheumatoid arthritis at age fifty, was placed on Fosimex and calcium supplements at the time of diagnosis. She was unable to tolerate the Fosimex due to stomach problems which readily developed into an ulcer. The subject was also "ultra sensitive" to various over-the-counter calcium and vitamin supplements, experiencing problems with nausea and/or stomach pain. The subject discontinued the use of Fosimex, calcium, and over-the-counter vitamins at this time. The first bone scan taken showed the subject had osteoporosis in the left hip, ward's triangle, trochanteric area and the L1, L2, L3 and L4 lumbar. Bone scans taken in subsequent third through fifth years showed little or no improvement.

During the beginning of the sixth year, the subject was prescribed two L3-Multi-Vitamin Supplements (i.e. two tablets) to gradually begin the calcium/vitamin regimen. After two weeks, the subject reported no stomach upset or sensitivity and an increase in her energy level. She began taking three to four L3-Multi-Vitamin Supplements per day.

At the end of the sixth year, a bone scan was performed on the subject. The scan indicated that the subject's lumbar (L1, L3, L4) had improved to the osetopenia level. The L2 lumbar was the only remaining lumbar still at the level of osteoporosis. There was improvement noted in the left hip, and the trochanteric hip area was in normal range. The bone scan concluded the subject was improving. The findings concluded that the subject had marked improvement in just eleven (11) months of taking L3-Multi-Vitamin Supplements. The subject's radiologist recommended continued medical management with the L3-Multi-Vitamin Supplements and follow-up examination in one to two years.

The results for this fifty-five year old subject led to the following conclusions:

1) L3-Multi-Vitamin Supplements contain the highest purity of ingredient and most absorbable form according to research.

2) The chewable formula of L3-Multi-Vitamin Supplements advances the absorption time for the calcium/vitamin supplements into the system through the teeth, gums, saliva and bones.

3) A healthy regimen of L3-Multi-Vitamin Supplements can enhance bone remineralization.

4) A healthy regimen of L3-Multi-Vitamin Supplements can improve osteoporosis.

5) A healthy regimen of L3-Multi-Vitamin Supplements, being the highest, purest, elemental calcium supplemental form, is easier for the stomach to tolerate than various over-the-counter vitamins.

6) A healthy regimen of L3-Multi-Vitamin Supplements can increase energy levels.

7) A healthy regimen of L3-Multi-Vitamin Supplements can improve a subject's overall health.

Case Study-2

Remineralization and Bone Enhancement

A sixty (60) year old white male subject, diagnosed with cancer, was planning to undergo chemo and radiation therapy. The subject was examined for oral health before starting therapies. Upon examination, the subject was diagnosed with bone loss between the roots of tooth #30. Due to studies showing the effects of chemo-therapy and radiation causing demineralization of the teeth and bones and the break down of the gums, the subject was prescribed L3-Multi-Vitamin Supplements in combination with fluoride applications as a protective/preventive measure.

Impressions were taken of the subject's upper and lower arch. Trays were made from the models. The subject was instructed to fill the trays with a sodium fluoride solution and to chew four (4) L3-Multi-Vitamin Supplements per day. The subject began the vitamin/fluoride regimen at this time.

Approximately eight months after beginning the L3-Multi-Vitamin Supplement regimen, the subject was presented for a hygiene appointment, x-ray and exam. Upon studying the x-ray and examining the subject, bone remineralization between the roots of tooth #30 was discovered. Although the subject had undergone and completed the chemo and radiation treatments, his oral health was excellent with positive sign of bone remineralization. The subject's gum tissue was in extremely good health. The subject continues to use the vitamin/fluoride regimen.

The results for this sixty year old subject led to the following conclusions:

1) L3-Multi-Vitamin Supplements include the highest purity of ingredients and are of the most absorbable form according to research.

2) The chewable formula of L3-Multi-Vitamin Supplements advances the absorption time for the calcium/vitamin supplements into the system through the teeth, gums, saliva and bones.

3) A healthy regimen combining the application of fluoride and chewing L3-Multi-Vitamin Supplements will enhance bone and tooth remineralization.

4) A healthy regimen combining the application of fluoride and chewing L3-Multi-Vitamin Supplements will enhance the health of gum tissue in the mouth.

5) A healthy regimen combining the application of fluoride and chewing L3-Multi-Vitamin Supplements is a protective/preventive measure recommended for subjects undergoing chemo-therapy and/or radiation. Subjects currently taking various prescribed medications also will benefit from this protective/preventive regimen for improved oral health.

Case Study-3

Remineralization and Bone Enhancement

An eighty-one (81) year old white female subject diagnosed with cancer had undergone surgery nine months prior to the beginning of her treatment with L3-Multi-Vitamin Supplements. The subject's oncologist had prescribed a preventive chemo drug taken daily as a precautionary measure. The subject was experiencing muscle cramps in her back and a lack of energy. The subject needed to continue the chemo drug, but wished to eliminate the muscle cramps and lack of energy.

At the end of the evaluation, the subject was prescribed a daily regimen of three L3-Multi-Vitamin Supplements for calcium/vitamin enhancement.

One month after the evaluation, the subject was evaluated and reported that her muscle cramps were gone, that she was out of pain, experiencing an increase in her energy level and feeling much better since beginning the L3-Multi-Vitamin Supplement regimen.

The results for this eighty-one year old subject led to the following conclusions:

1) L3-Multi-Vitamin Supplements include the highest purity of ingredients and are of the most absorbable form according to research.

2) The chewable formula of L3-Multi-Vitamin Supplements advances the absorption time for the calcium/vitamin supplements into the system through the teeth, gums, saliva and bones.

3) A healthy regimen of L3-Multi-Vitamin Supplements can help eliminate muscle pain and cramps.

4) A healthy regimen of L3-Multi-Vitamin Supplements can increase energy levels.

5) A healthy regimen of L3-Multi-Vitamin Supplements can improve overall health.

Case Study-4

Remineralization and Bone Enhancement

A sixty-eight (68) year old white female subject experiencing severe leg pain, could not walk even four feet without experiencing debilitating pain. She could not stand for any length of time without the recurring pain. She was not on medications and did not take any vitamin supplements.

At the end of the evaluation, the subject was prescribed three L3-Multi-Vitamin Supplements per day to begin a calcium/vitamin regimen.

Two weeks after the evaluation, the subject reported that she was feeling much better. She was free of leg pain, had an increased energy level, and could walk and stand without experiencing any pain. The subject continues on the L3-Multi-Vitamin Supplement regimen.

The results for this sixty-eight year old subject led to the following conclusions:

1) L3-Multi-Vitamin Supplements include the highest purity of ingredients and are of the most absorbable form according to research.

2) The chewable formula of L3-Multi-Vitamin Supplements advances the absorption time for the calcium/vitamin supplements into the system through the teeth, gums, saliva and bones.

3) A healthy regimen of L3-Multi-Vitamin Supplements can help eliminate muscle pain in the legs.

4) A healthy regimen of L3-Multi-Vitamin Supplements can increase energy levels.

5) A healthy regimen of L3-Multi-Vitamin Supplements can improve overall health.

Case Study-5

Remineralization and Bone Enhancement

An eighty-three (83) year old white female subject was experiencing severe leg cramps at night. She complained that she was being awoken four to five times nightly with cramps so severe that she must get up and move around to alleviate the pain. The subject was suffering from lack sleep and experiencing tiredness due from the interrupted sleep pattern.

At the end of the evaluation, the subject was prescribed three L3-Multi-Vitamin Supplements to begin a calcium/vitamin regimen. The subject was instructed to report back in a month.

One month after the evaluation, the subject reported that she was sleeping well and relieved of the leg cramps. She noticed an increase in her energy level as well, and was thrilled to be free of the leg pain and sleep interruptions, and felt great.

The results for this eighty-three year old subject led to the following conclusions:

1) L3-Multi-Vitamin Supplements contain the highest purity of ingredient and most absorbable form according to research.

2) A healthy regimen of L3-Multi-Vitamin Supplements can help eliminate muscle pain in the legs.

3) A healthy regimen of L3-Multi-Vitamin Supplements can help increase energy levels.

4) A healthy regimen of L3-Multi-Vitamin Supplements can improve overall health in general.

Case Study-6

Remineralization and Bone Enhancement

A fifty-one (51) year old white female subject was experiencing fatigue and sore muscles. She was healthy, ate well, exercised and took care of herself. She stated that she just did not have much energy. She had tried various vitamin supplements, but had not seen a difference in her energy level.

At the end of the evaluation, the subject was prescribed three to four L3-Multi-Vitamin Supplements to begin a calcium/vitamin regimen. The subject was instructed to report back in a month.

One month after the evaluation, the subject reported that she felt great, that her energy level had increased dramatically, and that she was no longer experiencing the muscle pain she was previously having before she began the L3-Multi-Vitamin Supplement regimen. She also stated that due to her increased energy level, she was been able to accomplish more in her job. The subject continues to take four L3-Multi-Vitamin Supplements daily.

The results for this fifty-one year old subject led to the following conclusions:

1) L3-Multi-Vitamin Supplements contain the highest purity of ingredient and most absorbable form according to research.

2) A healthy regimen of L3-Multi-Vitamin Supplements can help eliminate muscle pain.

3) A healthy regimen of L3-Multi-Vitamin Supplements can help increase energy levels.

4) A healthy regimen of L3-Multi-Vitamin Supplements can improve health in general.

Based upon the above-identified six exemplary case studies, it is apparent that the L3-multi-vitamin Supplement of the present invention provides vitamins and minerals for enhanced calcium absorption. The chewable form of the supplement provided herein specifically facilitates absorption of calcium in the teeth and bones of a subject, for enhanced physiological and psychological benefits. The L3-Multi-Vitamin Supplement is further beneficial for subjects experiencing osteoporosis, arthritis, demineralization of teeth and bones, bodily pain and lack of energy, as well as for the prevention of these ailments. It should also be noted that the L3-Multi-Vitamin Supplement of the present invention provides a source of additional calcium to subjects who require additional calcium due to lack thereof in their natural diet, as well as providing a source for balancing the amount of calcium in subjects who may have excess calcium in their diets or system.

Although particular embodiments and examples of the invention have been described in detail herein, it is to be understood that the invention is not limited to those particular embodiments and examples, and that various changes and modifications may be effected therein by on skilled in the art without departing from the scope or spirit of the invention as defined in the appended claims.

What is claimed is:

1. A method for dietary calcium supplementation, said method comprising the steps of:

supplementing a daily dietary regimen of a subject with a pharmaceutically acceptable composition including calcium citrate; and further supplementing the daily dietary regimen of the subject with:
   a) from approximately 200 IU to approximately 4000 IU of Vitamin A;
   b) from approximately 50 mg to approximately 1000 mg of Vitamin C;
   c) from approximately 40 IU to approximately 800 IU of Vitamin E;
   d) from approximately 10 mcg to approximately 200 mcg of Vitamin K;
   e) from approximately 5 mg to approximately 100 mg of Thiamin;
   f) from approximately 1.5 mg to approximately 30 mg of Riboflavin;
   g) from approximately 5 mg to approximately 100 mg of Niacin;
   h) from approximately 5 mg to approximately 100 mg of Pantothenic Acid;
   i) from approximately 40 mcg to approximately 800 mcg of Folate;
   j) from approximately 30 mg to approximately 600 mcg of Biotin;
   k) from approximately 10 mg to approximately 200 mg of Potassium;
   l) from approximately 5 mg to approximately 100 mg of Zinc;
   m) from approximately 20 mcg to approximately 400 mcg of Selenium;
   n) from approximately 0.2 mg to approximately 4 mg of Copper;
   o) from approximately 0.3 mg to approximately 6 mg of Manganese;
   p) from approximately 1 mg to approximately 20 mg of Vanadium;
   q) from approximately 0.1 mg to approximately 2 mg of Silica;
   r) from approximately 5 mg to approximately 100 mg of L-Lysine;
   s) from approximately 50 mg to approximately 1000 mg of bioflavanoids;
   t) from approximately 20 mg to approximately 400 mg of Ipriflavone;
   u) from approximately 9 mg to approximately 180 mg of Soy Isoflavones;
   v) calcium citrate comprising from approximately 100 mg calcium to approximately 2000 mg calcium;
   w) from approximately 50 mg magnesium to approximately 1000 mg magnesium;
   x) from approximately 50 mg to approximately 1000 mg of phosphorous;
   y) from approximately 40 IU to approximately 800 IU of Vitamin $D^3$;
   z) from approximately 0.3 mg to approximately 6 mg of boron;
   a1) from approximately 5 mg to approximately 100 mg of Vitamin $B^6$; and
   b1) from approximately 20 mcg to approximately 400 mcg of Vitamin $B^{12}$.

2. A method according to claim 1, wherein said steps of supplementing comprise supplementing a daily dietary regimen of the subject with:
   a) approximately 2000 IU of Vitamin A;
   b) approximately 500 mg of Vitamin C;
   c) approximately 400 IU of Vitamin E;
   d) approximately 100 mcg of Vitamin K;
   e) approximately 50 mg of Thiamin;
   f) approximately 15 mg of Riboflavin;
   g) approximately 50 mg of Niacin;
   h) approximately 50 mg of Pantothenic Acid;
   i) approximately 400 mcg of Folate;
   j) approximately 300 mcg of Biotin;
   k) approximately 100 mg of Potassium;
   l) approximately 50 mg of Zinc;
   m) approximately 200 mcg of Selenium;
   n) approximately 2 mg of Copper;
   o) approximately 3 mg of Manganese;
   p) approximately 10 mg of Vanadium;
   q) approximately 1 mg of Silica;
   r) approximately 50 mg of L-Lysine;
   s) approximately 500 mg of bioflavanoids;
   t) approximately 200 mg of Ipriflavone;
   u) approximately 90 mg of Soy Isoflavones;
   v) calcium citrate comprising approximately 1000 mg calcium;
   w) approximately 100 mg magnesium;
   x) approximately 500 mg of phosphorous;
   y) approximately 400 IU of Vitamin $D^3$;
   z) approximately 3 mg of boron;
   a1) approximately 50 mg of Vitamin $B^6$; and
   b1) approximately 200 mcg of Vitamin $B^{12}$.

3. A method according to claim 1, said composition being chewable for facilitating absorption in teeth and bones of the subject.

4. A multi-vitamin supplement for enhanced calcium absorption, said supplement comprising:
   a) from approximately 200 IU to approximately 4000 IU of Vitamin A;
   b) from approximately 50 mg to approximately 1000 mg of Vitamin C;
   c) from approximately 40 IU to approximately 800 IU of Vitamin E;

d) from approximately 10 mcg to approximately 200 mcg of Vitamin K;
e) from approximately 5 mg to approximately 100 mg of Thiamin;
f) from approximately 1.5 mg to approximately 30 mg of Riboflavin;
g) from approximately 5 mg to approximately 100 mg of Niacin;
h) from approximately 5 mg to approximately 100 mg of Pantothenic Acid;
i) from approximately 40 mcg to approximately 800 mcg of Folate;
j) from approximately 30 mg to approximately 600 mcg of Biotin;
k) from approximately 10 mg to approximately 200 mg of Potassium;
l) from approximately 5 mg to approximately 100 mg of Zinc;
m) from approximately 20 mcg to approximately 400 mcg of Selenium;
n) from approximately 0.2 mg to approximately 4 mg of Copper;
o) from approximately 0.3 mg to approximately 6 mg of Manganese;
p) from approximately 1 mg to approximately 20 mg of Vanadium;
q) from approximately 0.1 mg to approximately 2 mg of Silica;
r) from approximately 5 mg to approximately 100 mg of L-Lysine;
s) from approximately 50 mg to approximately 1000 mg of bioflavanoids;
t) from approximately 20 mg to approximately 400 mg of Ipriflavone;
u) from approximately 9 mg to approximately 180 mg of Soy Isoflavones;
v) calcium citrate comprising from approximately 100 mg calcium to approximately 2000 mg calcium;
w) from approximately 50 mg magnesium to approximately 1000 mg magnesium;
x) from approximately 50 mg to approximately 1000 mg of phosphorous;
y) from approximately 40 IU to approximately 800 IU of Vitamin $D^3$;
z) from approximately 0.3 mg to approximately 6 mg of boron;
a1) from approximately 5 mg to approximately 100 mg of Vitamin $B^6$; and
b1) from approximately 20 mcg to approximately 400 mcg of Vitamin $B^{12}$.

5. A multi-vitamin supplement according to claim 4, said supplement comprising:
a) approximately 2000 IU of Vitamin A;
b) approximately 500 mg of Vitamin C;
c) approximately 400 IU of Vitamin E;
d) approximately 100 mcg of Vitamin K;
e) approximately 50 mg of Thiamin;
f) approximately 15 mg of Riboflavin;
g) approximately 50 mg of Niacin;
h) approximately 50 mg of Pantothenic Acid;
i) approximately 400 mcg of Folate;
j) approximately 300 mcg of Biotin;
k) approximately 100 mg of Potassium;
l) approximately 50 mg of Zinc;
m) approximately 200 mcg of Selenium;
n) approximately 2 mg of Copper;
o) approximately 3 mg of Manganese;
p) approximately 10 mg of Vanadium;
q) approximately 1 mg of Silica;
r) approximately 50 mg of L-Lysine;
s) approximately 500 mg of bioflavanoids;
t) approximately 200 mg of Ipriflavone;
u) approximately 90 mg of Soy Isoflavones;
v) calcium citrate comprising approximately 1000 mg calcium;
w) approximately 100 mg magnesium;
x) approximately 500 mg of phosphorous;
y) approximately 400 IU of Vitamin $D^3$;
z) approximately 3 mg of boron;
a1) approximately 50 mg of Vitamin $B^6$; and
b1) approximately 200 mcg of Vitamin $B^{12}$.

6. A multi-vitamin supplement according to claim 4, said supplement being formulated for a subject having at least one of:
osteoporosis;
arthritis;
demineralization of teeth and bones;
bodily pain; and
lack of energy.

7. A multi-vitamin supplement according to claim 4, said supplement being chewable for facilitating absorption in teeth and bones of a subject.

* * * * *